(12) United States Patent
Davaris et al.

(10) Patent No.: US 6,858,016 B2
(45) Date of Patent: Feb. 22, 2005

(54) DEVICE FOR MONITORING CARDIAC COMPRESSION, RESUSCITATION MASK AND METHOD OF APPLYING CARDIAC COMPRESSION

(75) Inventors: Andrew Davaris, Caulfield North (AU); George Karlis, Burwood (AU)

(73) Assignee: MEDTEQ Holdings PTY LTD, Springwood (AU)

( * ) Notice: Subject to any disclaimer, the term of this patent is extended or adjusted under 35 U.S.C. 154(b) by 227 days.

(21) Appl. No.: 10/055,949

(22) Filed: Jan. 28, 2002

(65) Prior Publication Data

US 2002/0078954 A1 Jun. 27, 2002

Related U.S. Application Data

(63) Continuation of application No. PCT/AU00/00715, filed on Jun. 23, 2000.

(30) Foreign Application Priority Data

Aug. 3, 1999 (AU) .............................................. PQ1994

(51) Int. Cl.[7] .............................................. A61H 31/00
(52) U.S. Cl. ........................ 601/41; 601/44; 128/202.22
(58) Field of Search ........................ 128/202.28, 204.21, 128/205.25, 205.13, 204.28, 202.22; 601/41, 44

(56) References Cited

U.S. PATENT DOCUMENTS

| | | |
|---|---|---|
| 2,699,163 A | 1/1955 | Engstrom .................... 601/44 |
| 3,658,058 A | 4/1972 | Neidhart et al. ........ 128/201.18 |
| 4,019,501 A | 4/1977 | Harris ............................ 601/1 |
| 4,077,400 A | 3/1978 | Harrigan ........................ 601/1 |
| 4,196,725 A | 4/1980 | Gunderson ............. 128/205.25 |
| 4,326,507 A | 4/1982 | Barkalow .................... 601/106 |
| 4,355,634 A | 10/1982 | Kanter ......................... 601/41 |
| 4,397,306 A | 8/1983 | Weisfeldt et al. ............. 601/41 |
| 4,944,291 A | 7/1990 | Robertson, II et al. . 128/203.11 |
| 5,490,820 A | * 2/1996 | Schock et al. ................ 601/41 |
| 5,496,257 A | 3/1996 | Kelly ............................ 601/41 |
| 5,738,637 A | 4/1998 | Kelly et al. .................... 601/41 |
| 6,174,295 B1 * | 1/2001 | Cantrell et al. ............... 601/41 |
| 6,325,771 B1 * | 12/2001 | Kelly et al. .................... 601/41 |

FOREIGN PATENT DOCUMENTS

| | | |
|---|---|---|
| DE | 2321740 | 11/1974 |
| WO | WO 92/17234 | 10/1992 |
| WO | WO 94 26229 A | 11/1994 |

\* cited by examiner

*Primary Examiner*—Henry Bennett
*Assistant Examiner*—Mital Patel
(74) *Attorney, Agent, or Firm*—Oliff & Berridge, PLC

(57) ABSTRACT

Device (1) for monitoring cardiac compression being applied to a pateitn comprises a body to overlie and contact the sternum, preferably of width no greater than the width of the sternum. The device includes indidication means (9) responsive to the force applied to the body by the user for providing an indication of the cardiac compression applied to the sternum. Also disclosed is a resuscitation mask adapted to be place over the mouth of a patient, the mask includes a nostril closing means adapted to press against the sides of the nose to close the nostrils when the mask is sealed against the face of the patient.

8 Claims, 6 Drawing Sheets

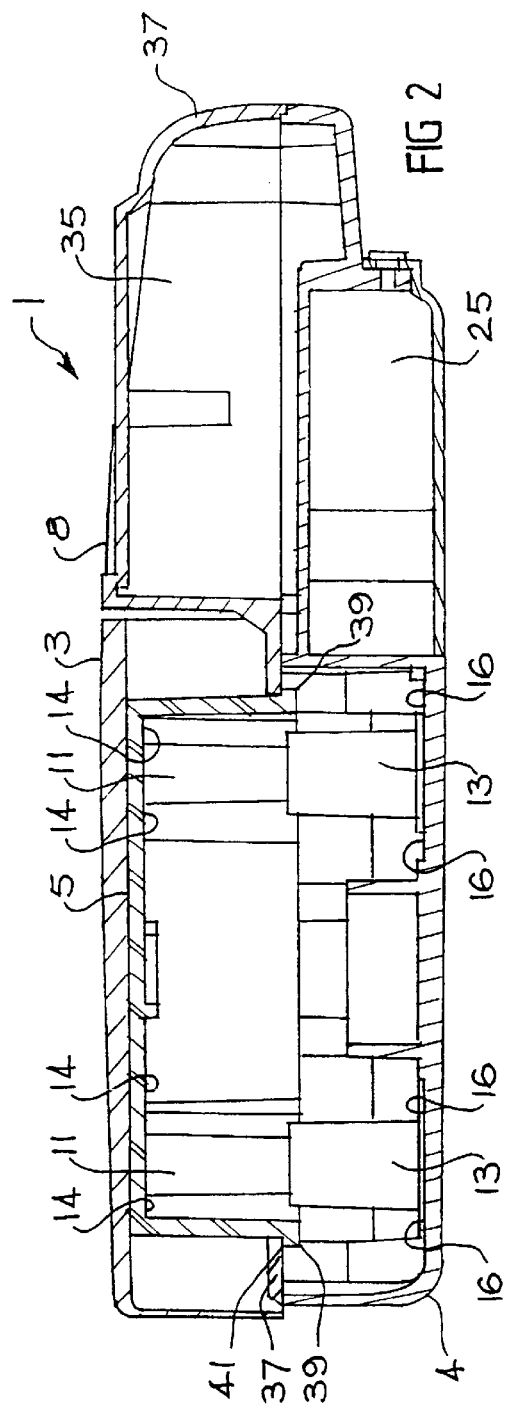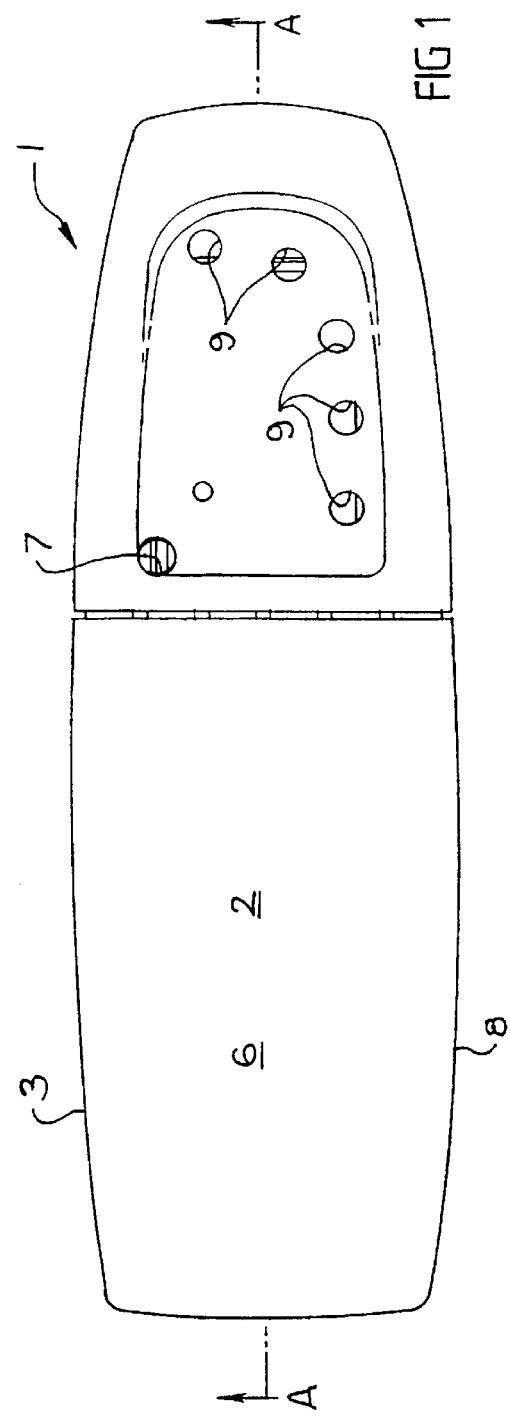

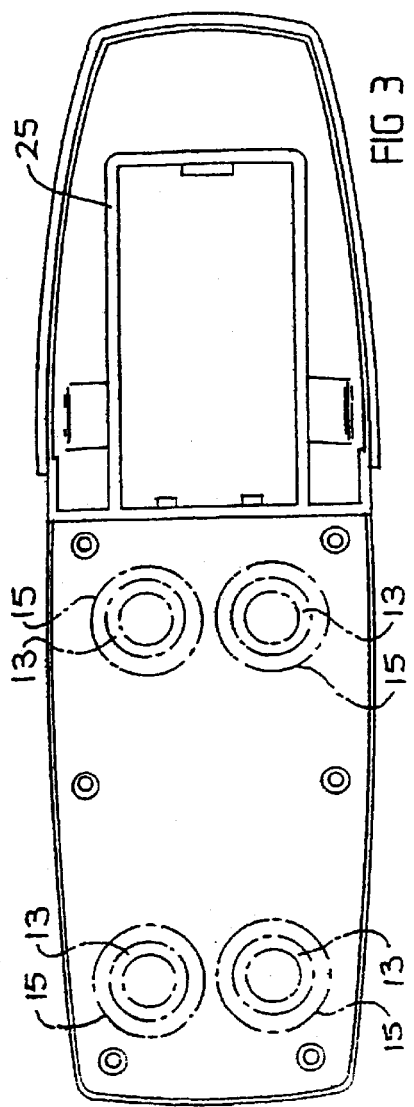
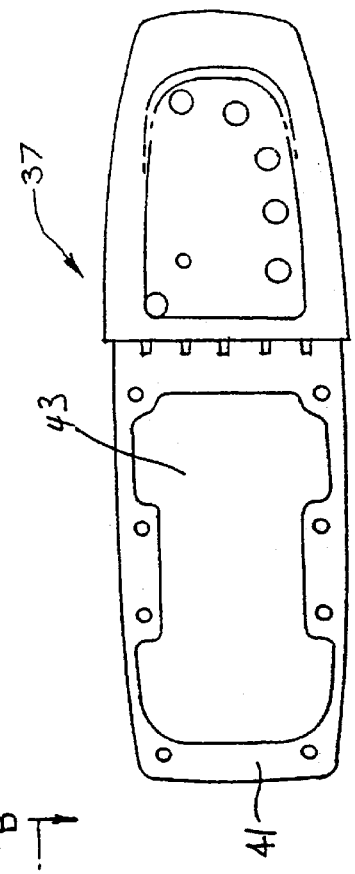
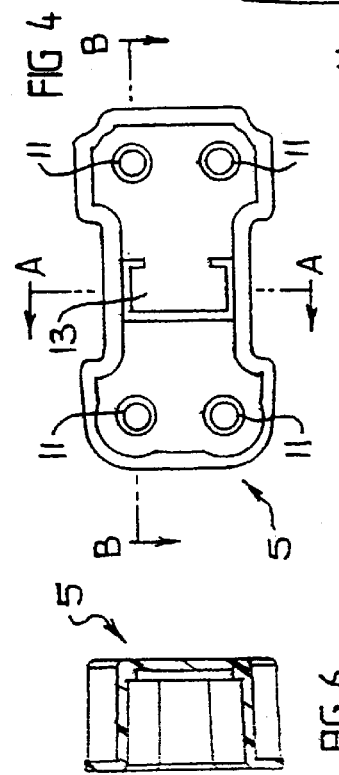
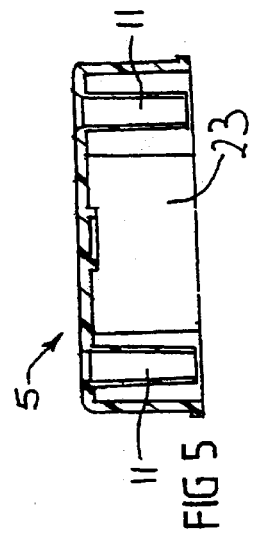

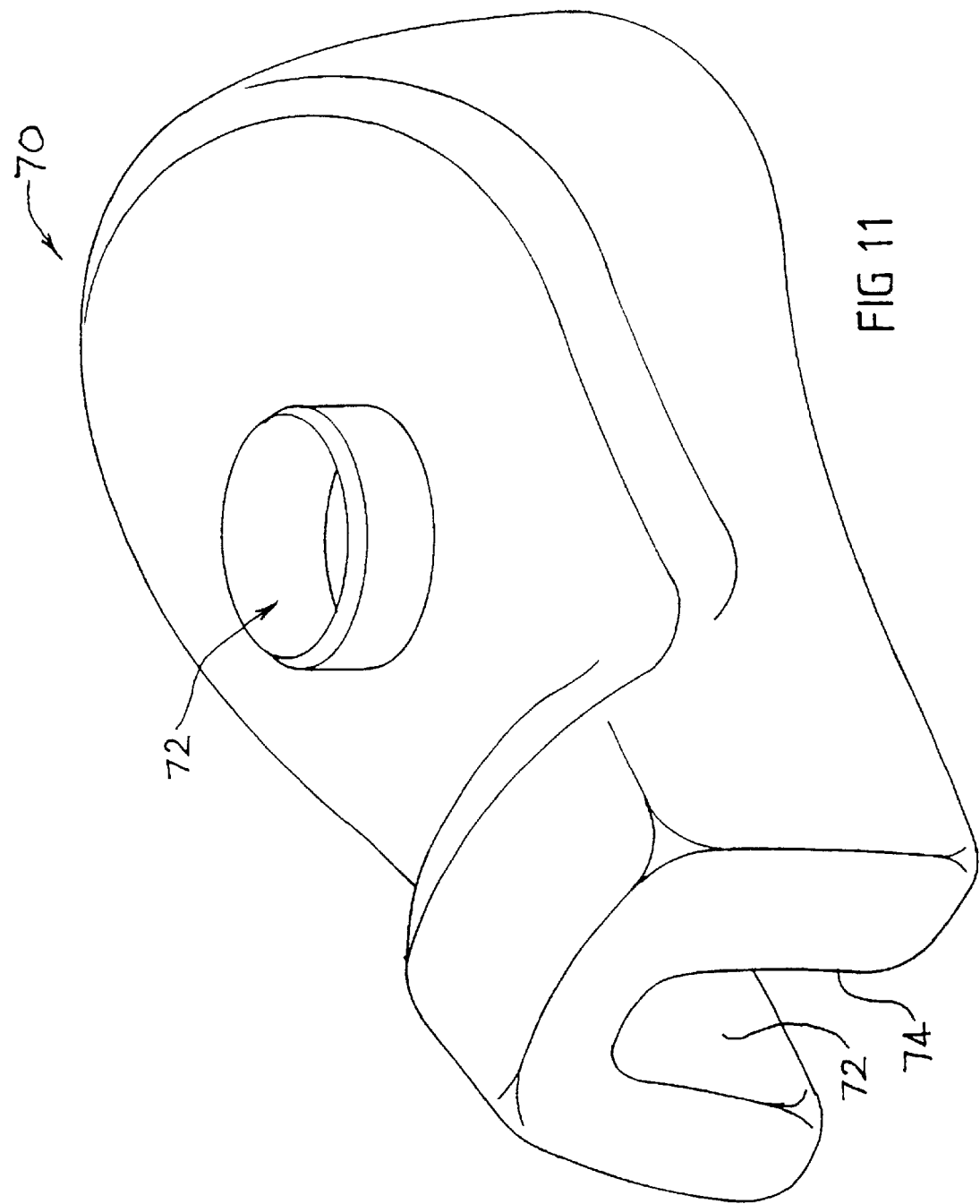

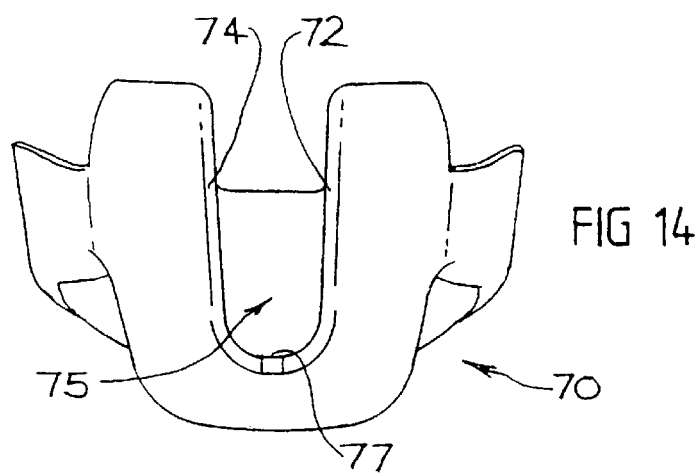
FIG 14
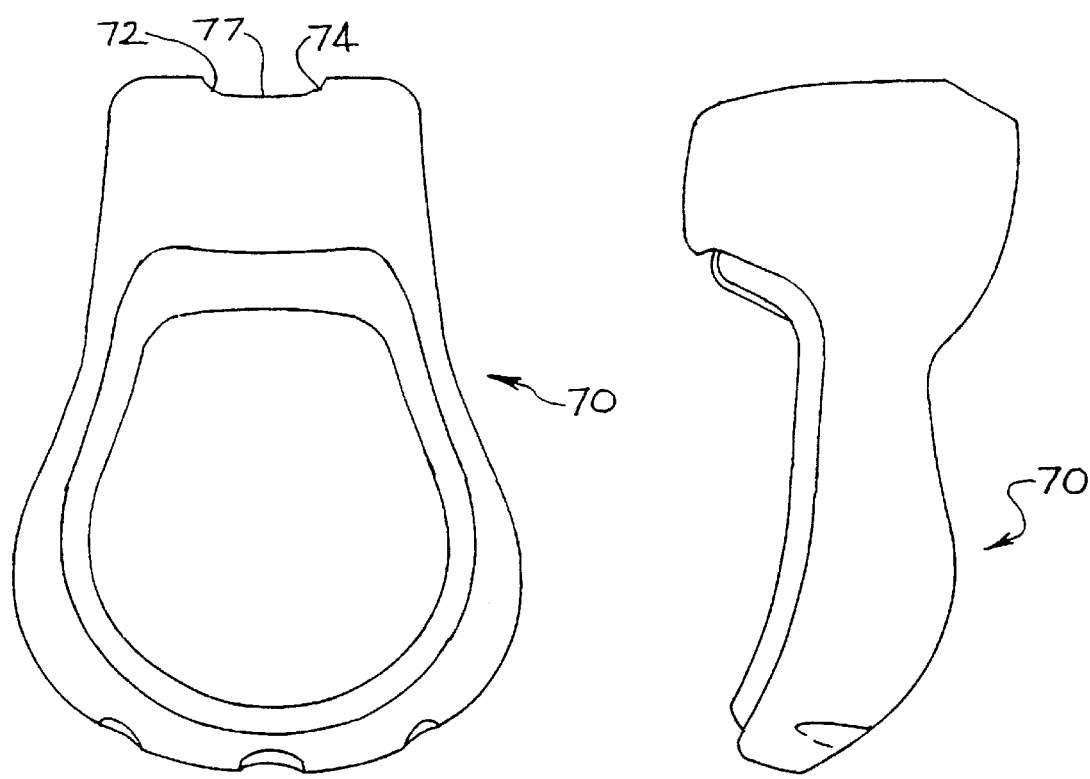
FIG 13
FIG 15

DEVICE FOR MONITORING CARDIAC COMPRESSION, RESUSCITATION MASK AND METHOD OF APPLYING CARDIAC COMPRESSION

This is a Continuation of Application No. PCT/AU00/00715 filed Jun. 23, 2000. The entire disclosure of the prior application(s) is hereby incorporated by reference herein in its entirety.

The present invention relates generally to methods and apparatus for use in cardio pulmonary resuscitation (CPR). More specifically the invention provides a device for monitoring cardiac compression being applied to a patient, a method of applying cardiac compression to a patient, a resuscitation mask, and a kit including a device for monitoring cardiac compressions and a resuscitation mask. The resuscitation mask may find broader application such as for use by anaesthetists during surgical procedures and the device for monitoring cardiac compression may also be used to train people in the application of cardiac compression.

DESCRIPTION OF RELATED ART

Each year a large number of persons suffer cardiac and/or respiratory failure. Most of these instances of cardiac and respiratory failure occur outside of the presence of trained medical personnel. However, it is important for CPR to be applied as soon as possible to provide the person who suffers cardiac and/or respiratory failure the best chance of surviving. Therefore, members of the public are encouraged to learn first aid skills and how to apply CPR in particular. While many members of the public may learn CPR at one time or another it may be a long time since they have applied CPR when they are actually confronted by a crisis which requires them to perform it. Furthermore, even if a person has trained in CPR relatively recently, the pressure of a crisis situation can cause even the most reliable of persons to perform below their best. It would therefore be advantageous to provide apparatus and methods to allow a person to better apply cardio and/or pulmonary resuscitation.

With reference to the need to apply cardiac compressions following heart failure it is important that cardiac compressions be applied with the correct pressure and preferably at the correct repetition rate. It is particularly difficult for a person who has learnt how to apply cardiac compressions some time ago to know whether they are applying sufficient force to the sternum of the patient and thus the heart. If too little pressure is applied, there will be insufficient compression of the heart to have the desired effect, whereas too much pressure can lead to broken ribs or a broken sternum and hence impaired breathing. Furthermore, if the patient's ribs are broken when CPR is applied this causes additional complications when the patient is taken to hospital. Damage to the patient's rib cage may be caused not only by excessive application of force but also by inaccurate application of force where force is not applied to the sternum but rather to the surrounding rib area. Accordingly, it would be an advantage to provide a method and/or apparatus to enable more effective application of cardiac compression.

Resuscitation masks are known which fit over and surround both the nose and the mouth of the patient and seal against the patient's face whereafter a source of oxygen such as pure oxygen or air can be introduced through a passage through the mask into the area surrounding the patients nose and mouth or through a tube directly into the patient's mouth. Such masks are relatively large and cumbersome to use and require two hands to be held in place properly.

An alternative type of mask is disclosed in international patent application having publication number WO 92/17234 in the names of George Karlis and Andrew Davaris. This mask is adapted to overlie the mouth of a patient and to press against the open ends of the nostril passages of the patient to thereby seal against those open ends of the nostril passages when the mask is in position. As with the large type of mask, the aim of the smaller mask which presses against the open ends of the nostril passages is to ensure that the only fluid which passes to and from the patient passes through the mouth. This mask with portions which press against the open ends of the nostril passages has a disadvantage in that where the patient's nostrils are subject to flaring, as is genetically inherent among some racial groups, the mask will not seal the nostrils effectively and therefore fluid will be able to pass undesirably through the nostrils. It would therefore be advantageous to provide a mask which is both relatively small and seals the nostrils of the patient more effectively.

SUMMARY OF INVENTION

In a first aspect, the invention provides a device for monitoring cardiac compression being applied to a patient, said device including:
  a body adapted to overlie and contact the chest of a patient and to which a user can apply force to provide cardiac compressions to said patient; and
  indication means responsive to the force applied to said body by said user for providing an indication to said user of cardiac compression applied to said patient so that said user can monitor said cardiac compression.

Preferably said indication means indicates to said user whether the force applied to said body is providing adequate cardiac compression to said patient.

Preferably said indication means is capable of indicating a plurality of levels of cardiac compression, each said level of cardiac compression corresponding to cardiac compression suitable for patients of different ages and or sizes.

Preferably said device includes compression regulation means for regulating the rate at which cardiac compressions are applied by instructing the user when to apply cardiac compressions.

Preferably said cardiac compression regulation means is a signal which is repeated at regular intervals. Preferably said regular intervals correspond with a desirable rate of application of cardiac compression.

If said indication means is a visual indication means it is preferred that the compression regulation means be an aural indication means such as an audible beep.

In one embodiment the aural indication means can provide an audible instruction such as "press" or a count of the neither of compressions that have been applied. This last embodiment is particularly useful to remind the user that they must perform a separate task, such as providing breaths of air to the patient, after a certain number of compressions. Alternatively or in addition, there may be provided a secondary indication means, for example a visual, or more preferably, an audible tone or message which acts as a cue to the user to perform some additional function, such as administering breaths to the patient.

In a second aspect the invention provides a resuscitation mask adapted to be placed over the mouth of a patient, said mask having:
  a fluid passage;
  sealing means for sealing the mask against the face of said patient when the mask is placed over the mouth of the patient so that fluid moving to and from the patient's mouth moves predominantly through said fluid passage; and nostril closing means adapted to press against the sides of patient's nose and deflect the flesh around the nostril openings to close the nostrils of said patient when said mask is sealed against the face of said patient.

Preferably said fluid passage extends into the mouth of said patient when said mask is sealed against the face of said patient so that it is preferably located between the teeth of the patient.

In a third aspect the invention provides a method of applying cardiac compression to a patient including:

providing a body sized to have a width substantially no greater than the width of a patient's sternum;

locating said body over a patient's sternum; and applying force to said body to thereby provide cardiac compression to said patient.

Preferably said method of applying cardiac compression includes the further step of providing an indication to said user of cardiac compression applied to said patient so that said user can monitor said cardiac compression.

Preferably said method further includes the step of regulating the rate of which cardiac compressions are applied to said patient by providing means to instruct said user as to when to apply cardiac compressions.

In a fourth aspect the invention provides a kit including a resuscitation mask and a device for monitoring cardiac compressions, the resuscitation mask being adapted to be placed over the mouth of a patient and having:

a fluid passage;

sealing means for sealing the mask against the face of said patient when the mask is placed over the mouth of the patient so that fluid moving to and from the patient's mouth moves predominantly through said fluid passage; and nostril closing means adapted to press against the sides of a patients nose and deflect the flesh around the nostril openings to close the nostrils of said patient when said mask is sealed against the face of said patient, said device having:

a body adapted to overlie and contact the chest of a patient and to which a user can apply force to provide cardiac compressions to said patient; and indication means responsive to the force applied to said body by said user for providing an indication to said user of cardiac compression applied to said patient so that said user can monitor said cardiac compression.

BRIEF DESCRIPTION OF THE DRAWINGS

Examples of embodiments of the invention will now be described with reference to the accompanying drawings in which:

FIG. 1 is a top view of an embodiment of a device for monitoring cardiac compression;

FIG. 2 is a cross-section taken through line A—A in FIG. 1;

FIG. 3 is a cut away plan view of the device;

FIG. 4 shows a plunger of the device;

FIG. 5 is a cross-sectional view along line B—B of FIG. 5;

FIG. 6 is a cross-sectional view along line A—A of FIG. 4;

FIG. 11 shows a resuscitation mask of an embodiment of the invention;

FIG. 13 is a top view of the resuscitation mask;

FIG. 14 is an end view of the resuscitation mask;

FIG. 15 is a side view of the resuscitation mask; and

FIG. 16 is a plan view of an electronics cover for the device.

DETAILED DESCRIPTION OF PREFERRED EMBODIMENTS

Figure 10:
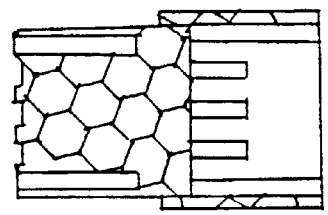
FIG. 10 is a cross-section through line A—A of FIG. 9.
Figure 9:
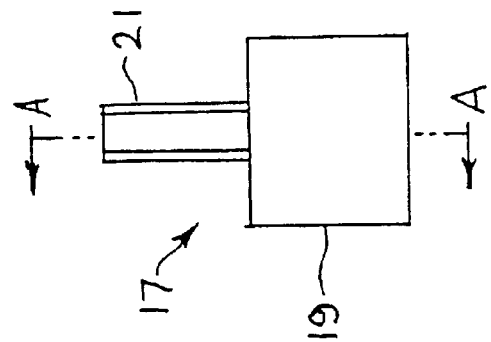
FIG. 9 is a side view of the contact block.
Figure 8:
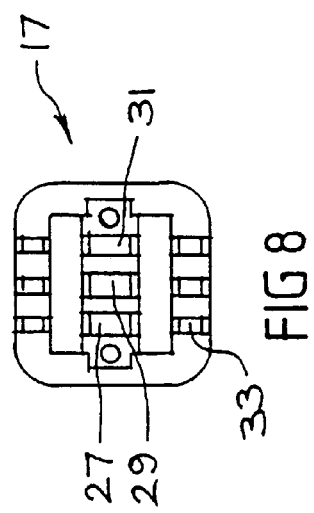
FIG. 8 is a top view of the contact block.
Figure 7:
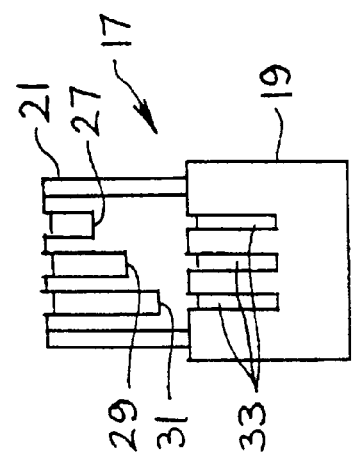
FIG. 7 is a front view of a contact block which forms part of the device.

FIG. 1 shows a device 1 for monitoring cardiac compressions according to an example of an embodiment of the invention. The size of the device 1 is such that it can be located over a patient's sternum. Typically the size of the device 1 is such that its width is no greater than the width of a patients sternum. When the device 1 is in position overlying the sternum of a patient so that the length of the device lies along the length of the sternum and the width of the device extends across the sternum, a person can apply cardiac compressions to the patient by applying force to the body 8 of the device 1. That is to say, by locating the device 1 over the patient's sternum and applying force to the body 8, the user can ensure that no force is applied to the patient's ribs, thereby reducing the risk of breaking ribs which causes surgical complications in resuscitated patients. The user can monitor the application of cardiac compressions by applying cardiac compressions to area 2 of the upper surface 6 of the device 1 which is part of cover 3. The cover is moveable relative to the base 4 so that it can move towards the base 4 and overlies a plunger 5. In the illustrated embodiment the plunger 5 is formed separately from the cover 3, however such construction need not be adopted in all embodiments.

The plunger 5 has four spigots 11 which fit within, and are telescopically slideable relative to, corresponding sockets 13 in the base 4. Four coil springs 15 provide a biasing means and are located around both the spigots 11 and the sockets 13 and prevent the plunger 5 from moving towards the base 4 unless a force is applied to the cover 3. That is to say, the coil springs abut the inner surfaces 14 of the plunger and the inner surfaces 16 of the base such as to urge the plunger 5 and the base 4 apart. The four spring arrangement is chosen so that uneven application of force to the cover 3 will not result in uneven translation of the centre region of the plunger 5 relative to the base 4.

In the illustrated embodiment, the device is constructed by first locating the spigots 11 of the plunger 5 within the coil springs 15 and sockets 13 and then locating the electronics cover 37 in place so that a plate portion 41 of an electronics cover 37, which has a cut-out region 43 designed to receive the plunger 5, overlies flange 39 of the plunger 5, thereby trapping the plunger within the plate portion 41. This not only prevents the plunger 5 from moving vertically past the plate portion 41 but also prevents lateral movement of the plunger, thereby lending stability to the construction of the device. The device 1, is configured such that translation of the plunger 5 relative to the base is indicative of the cardiac compression applied to the patient so that a user can monitor the cardiac compression which is applied.

In the preferred embodiment, indication means are provided by calibrating the strength of the springs relative to the movement of the plunger 5 towards the base 4. This movement is measured by contact member 17 which is located roughly in the middle of the plunger with the moveable portion 21 of the contact member 17 being received within contact block receiving means 23 in the plunger 5. The contact block 17 consists of a moveable portion 21 and a fixed portion 19 which are biased relative to one another by a biasing means in the form of a spring (not shown). Thus, when the plunger 5 is moved relative to the base 4, the moveable part of the contact block 21 is moved relative to the fixed part of the contact block 19. The moveable portion of the contact block has, first, second and third contacts 27, 29 and 31 which are different lengths such that depending on the amount of translation of the plunger, one or more of these contacts 27, 29 and 31 will come into contact with fixed electrical contact 33. In the illustrated embodiment there are three contacts of varying lengths, although obviously additional contacts could be provided. Depending on which contacts contact the fixed contact 33 the electrical circuit will be altered. Known electronics which are stored in cavity 35 operate the various different indicating means 9 in the form of lights 9, depending on which contacts are closed. In the most simple arrangement, a single light 9 will light when one contact is closed, two lights will light when two contacts are closed, and three light will light when three contacts are closed etc, up to the preferred number of five lights.

A power light 7 indicates when the device is operating. The device 1 is preferably calibrated such that the number of lights 9 which light in response to translation of the plunger correspond to the amount of force applied to the patient. Preferably, a first light will light when the amount of force applied corresponds to the force that should be applied to a small child, a second light will light when the force corresponds to the force that the should be applied to a normal adult and a third light lights which corresponds to the force which should be applied to a large adult. Thus, as the user presses on the cover 3 to apply cardiac compressions to a patient, the user can tell whether they are providing insufficient, adequate or excessive cardiac compression by the number of lights which are lit and modify the force which they apply to the covers, and hence the patient, so that it matches the correct amount of cardiac compression for the patient.

Further electronics which can be constructed according to known techniques are provided within electronic cavity 35, such that, when activated, the device provides an audible noise, such as a beep, corresponding to the rate at which compressions should be applied. That is to say, the audible sound provides a rhythm which enables a person applying cardiac compression to apply compressions at a regular and appropriate interval. It has been found that the presence of an audible beep allows users of the device to keep a much better rhythm than they would normally without the presence of a beep. While providing an audible beep is the preferred method of instructing the user to applying compressions, it is obvious that other systems could be used. For example, in an alternative embodiment synthesised voice commands are provided by the electronics to instruct the user when to apply compressions. The electronics could also count the number of compressions which have been applied, such that if the user of the device needs to provide breaths of air to the patient at particular intervals, they can be reminded as to when to provide them. For example, the device may count the user through providing twenty heart compressions followed by three breaths or similar.

FIG. 11 shows a resuscitation mask 70 according an example of an embodiment of the invention. The resuscitation mask 70 has a fluid passage 72 therethrough so that when the mask 70 overlies the mouth of patient, fluid, such as oxygen can be introduced to the region around the patients mouth.

The resuscitation mask 70 has nostril closing means in the form of a pair of abutment surfaces 72 and 74, such that when the mask is located over the face of the patient in use, the patient's nose is received in the channel 75 region between the pair of abutment surfaces 72 and 74 which abut the sides of a patient's nose. The channel is defined by abutment surfaces 72 and 74 and nose 6 bridging portion 77. The resuscitation mask 70 is made of a resilient material and the space between the abutment surfaces sized such that the abutment surfaces 72, 74 will press on sides of the patient's nose and deflect the flesh around the nostril openings to close the patient's nostrils. In this manner when the resuscitation mask is sealed against the patient's face, the patient's nose will also be sealed, thereby ensuring that fluid flows into that patient via the patient's mouth rather than via the patient's nostrils.

Figure 12:
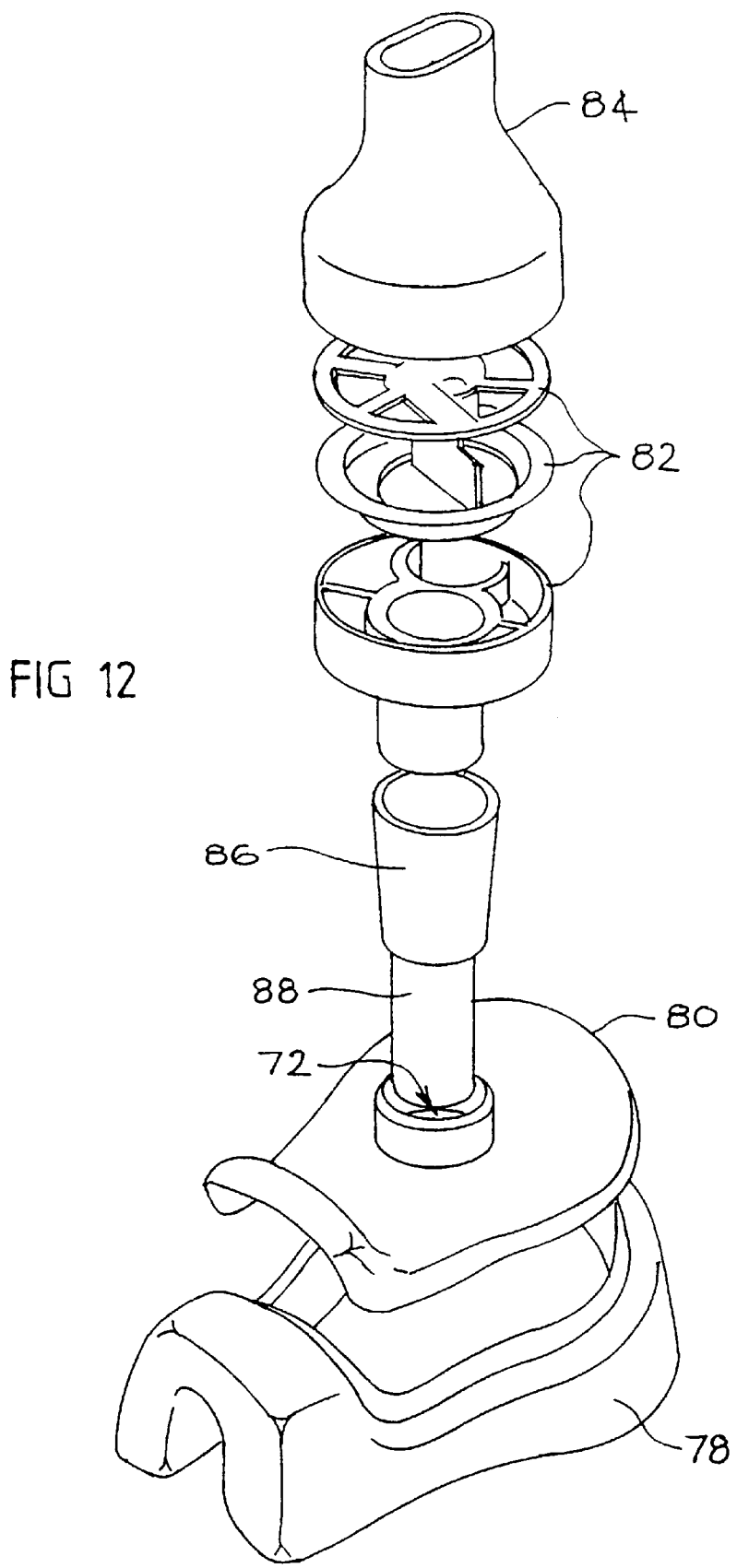
FIG. 12 is an exploded view of a resuscitation mask in conjunction with a fluid passage for use with the resuscitation mask.

As shown in FIG. 12 the resuscitation mask 70 is typically formed of a two part construction of a sealing portion 78 and a cover portion 80. The cover portion is typically clear to allow the patient's mouth to be viewed through the mask 70. As shown in FIG. 12, the resuscitation mask 70 is adapted to be used with further fluid passage elements though which, when assembled, a user can introduce air into a patient's mouth. The fluid passage elements include a mouth piece 84, several baffle elements 82 to prevent material from the patient's mouth from entering the user's mouth, and a patient mouth Piece 86 designed to pass through fluid passage 72 such that dental portion 88 of the patient's mouth piece 86 sits between the patient's teeth when the mask is sealed against the face of the patient.

The mask 70 is sized such that the distance between the fluid passage 72 and the nose sealing portion corresponds substantially to the distance between extremities of a person's supper teeth and the base of the patient's nose to ensure that at least part of the abutment surfaces 72, 74 abut against the side of the patient's nose. It is to be noted that the distance between the patient's teeth and the base of the nose is fairly consistent from person to person.

As can be seen particularly from FIGS. 14 and 15, the profile of the resuscitation mask 70 is designed to correspond with the profile of a patient's face, to ensure a good seal between the sealing portion 78 and the patient's face. This is aided by the resilience of the material of the sealing portion 78 which allows the mask to be deformed to some extent relative to the patient's face.

In a particularly preferred embodiment the device for monitoring cardiac compressions 1 and the resuscitation mask 70 are provided in a single kit. Where only one person is available to apply CPR the elements combine advantageously to allow such a single user to apply CPR effectively. Typically when a single person applies CPR they apply a number of cardiac compressions followed by a number of breaths before resuming applying cardiac compressions and applying further breaths etc. It is important for both the device and the mask to be maintained in the correct location for them to have the intended effect. While the design of the mask 70 is such that it includes some means to hold it in place, in particular the abutment surfaces 72, 74 which engage the patient's nose, the device for applying cardiac compressions can easily move out of location while a user is applying breaths to the mask. However, the resuscitation mask 70 is advantageously sized such that it can be held in place by one hand while the user applies breaths, this allows the user to maintain the device 1 in position with their own hand so that they can readily begin reapplying cardiac compressions following completion of the application of breaths or alternatively to hold the mask in place with one hand and apply cardiac compressions via the cardiac device with the other hand. This latter procedure may require special training of an operator however, it is not outside of the scope of operation of both the mask and the cardiac device.

It will be obvious to those skilled in the art that modifications can be made to the present invention without departing from the spirit of the invention and such modifications are considered to be within the scope of this invention. For example, the face mask need not be formed with a mere passage therethrough, but could be formed integrally with a tube which could be attached to respiratory equipment such as a regulated oxygen supply. Furthermore, it should be noted that the device for applying cardiac compressions to a person, acts as guidance aid to ensure that force is applied to the right area of a patient's body. Thus, without providing an indication as to the strength of the compressions, the method of using such a guidance aid to ensure that force is applied to the right location has advantages over the prior art method of the user applying force with their hands directly to the patients.

What is claimed is:

1. A device for monitoring cardiac compression being applied to a patient, said device comprising:

a body adapted to overlie and contact the sternum of a patient; and having thereon a plurality of guide recipients;

a force receiving member overlying a portion of said body and moveable relative thereto and a force receiving platform on said force receiving member adapted to receive compressive force from a user;

a plurality of guide means on said force receiving member which cooperate with said plurality of guide recipients on said body;

biasing means to urge said force receiving member away from said body;

a plurality of pairs of contacts, one of each pair of contacts being located on said body and the other of said pair of contacts being located on said force receiving member, and wherein different pairs of contacts close when different amounts of force are applied to said force receiving member;

indication means responsive to the force applied to said force receiving member by the user for providing an indication to the user of said cardiac compression applied to the sternum; and compression regulation means for regulating the rate at which cardiac compressions are applied by instructing the user when to apply cardiac compression.

2. A device according to claim 1 wherein one of each pair of contacts is located on a guide means and the other of each pair of contacts is located on a corresponding guide recipient, and there is provided a biasing means with each guide means and corresponding guide recipient such that force applied to said force receiving member is transmitted relatively evenly to said body.

3. A device according to claim 2 wherein said biasing means is calibrated such that known force applied to the force receiving member corresponds to a known movement of the force receiving member relative to the body.

4. A device according to claim 3 wherein said guide means and guide recipients are either of spigots or sockets which move telescopically relative to each other.

5. A device according to claim 4 wherein each pair of co-operating spigots and sockets include a biasing means to bias the force receiving member away from the body.

6. A device according to claim 5 wherein each biasing means is a spring located around each spigot and socket.

7. A device according to claim 6 wherein there are a plurality of spigots and sockets spaced about the periphery of said force receiving member and body such that uneven application of force to the force receiving member does not result in uneven translation of force to the body.

8. A device according to claim 7 wherein there are four pairs of spigots and sockets.

* * * * *